(12) United States Patent
Kim et al.

(10) Patent No.: US 7,696,351 B2
(45) Date of Patent: Apr. 13, 2010

(54) PROCESS FOR THE PREPARATION OF S-(+)-CLOPIDOGREL BY OPTICAL RESOLUTION

(75) Inventors: Jae-Sun Kim, Suwon-si (KR); Nam Ho Kim, Seongnam-si (KR); Nam Kyu Lee, Suwon-si (KR); Jin Young Lee, Suwon-si (KR)

(73) Assignee: SK Chemicals Co., Ltd., Gyeonggi-do (KR)

( * ) Notice: Subject to any disclaimer, the term of this patent is extended or adjusted under 35 U.S.C. 154(b) by 43 days.

(21) Appl. No.: 12/159,145

(22) PCT Filed: Dec. 20, 2006

(86) PCT No.: PCT/KR2006/005600

§ 371 (c)(1),
(2), (4) Date: Sep. 3, 2008

(87) PCT Pub. No.: WO2007/074995

PCT Pub. Date: Jul. 5, 2007

(65) Prior Publication Data

US 2009/0275755 A1    Nov. 5, 2009

(30) Foreign Application Priority Data

Dec. 26, 2005 (KR) ................... 10-2005-0129717

(51) Int. Cl.
*C07D 495/04* (2006.01)

(52) U.S. Cl. .................................................. 546/114
(58) Field of Classification Search ............... 546/114
See application file for complete search history.

(56) References Cited

U.S. PATENT DOCUMENTS

| 4,529,596 | A | 7/1985 | Aubert et al. |
| 4,847,265 | A | 7/1989 | Badorc et al. |
| 5,204,469 | A | 4/1993 | Descamps et al. |
| 6,800,759 | B2 | 10/2004 | Valeriano et al. |
| 2002/0177712 | A1 | 11/2002 | Pandey et al. |

FOREIGN PATENT DOCUMENTS

| EP | 0 466 569 A | 1/1992 |
| EP | 0 466 569 B1 | 4/1996 |
| WO | WO 98/51689 | 11/1998 |
| WO | WO 99/18110 | 4/1999 |
| WO | WO 02/059128 | 8/2002 |
| WO | WO 03/066637 A | 8/2003 |
| WO | WO 2005/063708 A | 7/2005 |

*Primary Examiner*—Patricia L Morris
(74) *Attorney, Agent, or Firm*—Frommer Lawrence & Haug LLP; Ronald R. Santucci

(57) ABSTRACT

The present invention relates to a process for the preparation of S-(+)-clopidogrel by an optical resolution and, more particularly, to a process for the preparation of S-(+)-clopidogrel represented by the following formula 1 with high optical purity by converting a clopidogrel racemic carboxylic acid into a diastereomeric salt using a (+)-cinchonine for optical resolution, extracting an S-(+)-clopidogrel carboxylic acid from the diastereomeric salt using a suitable solvent under an acidic condition and then reacting the S-(+)-clopidogrel carboxylic acid with methanol.

12 Claims, No Drawings

PROCESS FOR THE PREPARATION OF S-(+)-CLOPIDOGREL BY OPTICAL RESOLUTION

This application is a 371 of PCT/KR2006/005600 filed on Dec. 20, 2006, published on Jul. 5, 2007 under publication number WO 2007/074995 A1 which claims priority benefits from South Korean Patent Application Number 10-2005-0129717 filed Dec. 26, 2005, the disclosure of which is hereby incorporated by reference.

TECHNICAL FIELD

The present invention relates to a process for the preparation of S-(+)-clopidogrel by an optical resolution and, more particularly, to a process for the preparation of S-(+)-clopidogrel represented by the following formula 1 with high optical purity by converting a clopidogrel racemic carboxylic acid into a diastereomeric salt using a (+)-cinchonine for optical resolution, extracting an S-(+)-clopidogrel carboxylic acid from the diastereomeric salt using a suitable solvent under an acidic condition and then reacting the S-(+)-clopidogrel carboxylic acid with methanol.

BACKGROUND ART

[Formula 1]

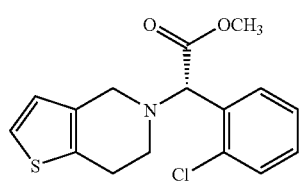

The chemical name of the S-(+)-clopidogrel represented by formula 1 is methyl (+)-(S)-α-(o-chlorophenyl)-6,7-dihydrothieno[3,2-a]pyridine-5-(4H)-acetate and has been known as an efficacious therapeutic agent for vascular system diseases used for the treatment of peripheral arterial diseases, such as cerebral apoplexy, thrombus, embolus etc., and coronary arterial diseases, such as myocardial infarction, angina pectoris, etc., as it shows a strong platelet aggregation inhibitory activity and an antithrombotic activity.

According to recent researches, it has been shown that the S-(+)-clopidogrel is a very effective agent inhibiting platelet aggregation because it has a strong inhibitory effect against the platelet aggregation even with a small dose compared with aspirin while it minimizes the toxic effects to be given on the gastrointestinal tract.

The S-(+)-clopidogrel is commercially available in the name of "Plavix®" and the tablet of this product contains approximately 98 mg of S-(+)-clopidogrel hydrogen sulphate and approximately 75 mg of S-(+)-clopidogrel base as an active ingredient.

As general processes for the preparation of clopidogrel, the preparation processes disclosed in the U.S. Pat. Nos. 4,529,596, 4,847,265 and 5,204,469 are summarized and represented by the following scheme 1.

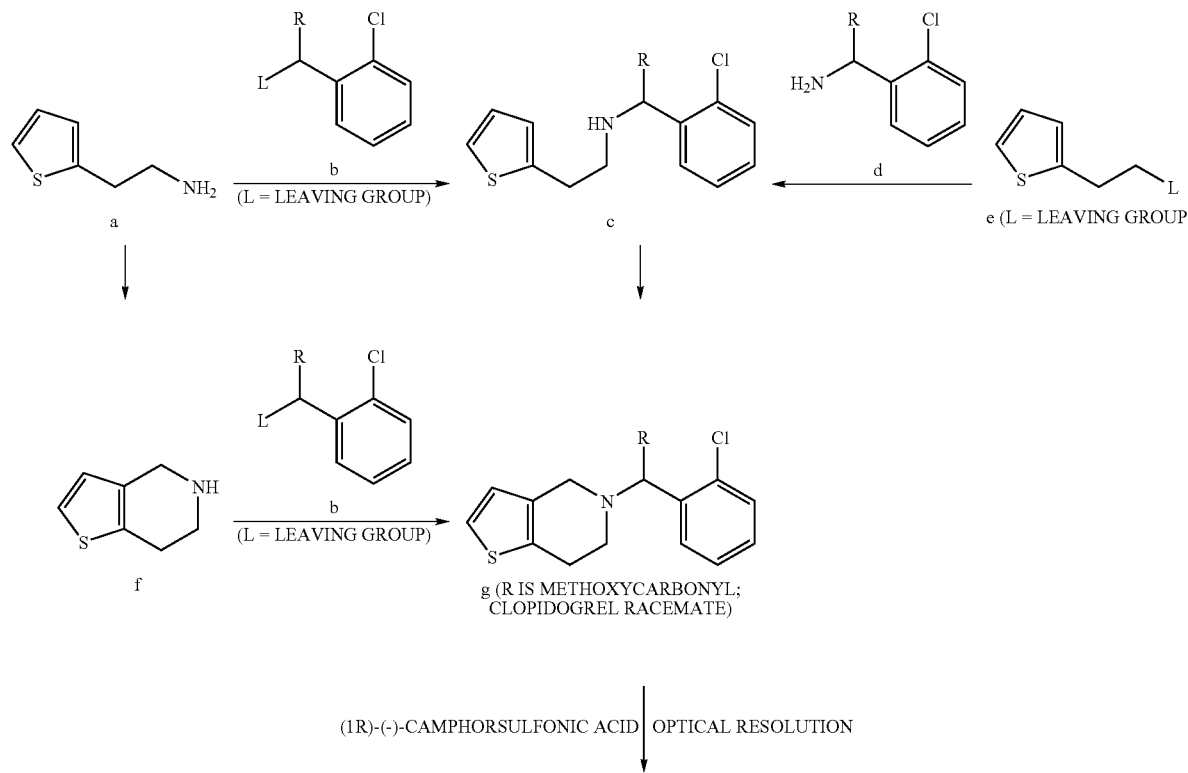

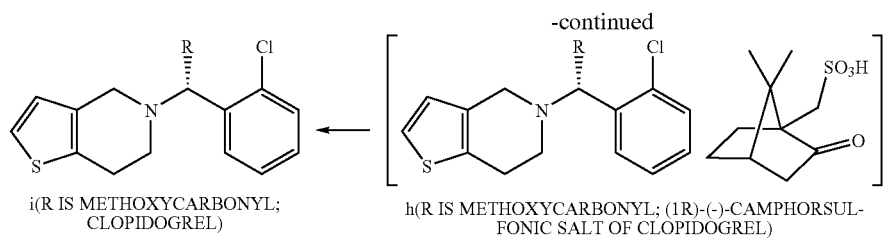

i(R IS METHOXYCARBONYL; CLOPIDOGREL)

h(R IS METHOXYCARBONYL; (1R)-(-)-CAMPHORSUL-FONIC SALT OF CLOPIDOGREL)

According to the processes of the conventional methods disclosed in scheme 1, there is required a continuous optical resolution process of forming a diastereomeric salt (h) by reacting a clopidogrel racemate (g) with an optically active acid, obtaining a pure diastereomeric salt of a dextrorotatory (R) optical isomer containing no levorotatory (L) optical isomers by recrystallization, and subsequently removing the optically active acid to prepare the S-(+)-clopidogrel as an optically pure dextrorotatory isomer.

U.S. Pat. No. 4,847,265 discloses an optical resolution method for the preparation of S-(+)-clopidogrel using a (1R)-(−)-camphorsulfonic acid as an optically active acid. International Patent Publication No. WO 98/51689 discloses a process for the preparation of S-(+)-clopidogrel by performing an optical resolution and subsequent reactions from a compound of formula (e) in scheme 1, wherein R is a nitrile, carboxamide, or carboxylic acid. Moreover, International Patent Publication No. WO 02/059128 discloses a process for the preparation of S-(+)-clopidogrel by carrying out an optical resolution and subsequent reactions from a compound of formula (g) in scheme 1, wherein R is a nitrile, carboxamide, or carboxylic acid.

As described above, the known processes for the preparation of S-(+)-clopidogrel may involve the optical resolution inevitably in a specific step of the continuous preparation processes. However, the optical resolution process of the clopidogrel racemate and an intermediate thereof is very disadvantageous environmentally or economically since it is unavoidable that, as for the levorotatory isomer, at least 50% of the intermediate is wasted. Moreover, in performing the optical resolution process to obtain an optical isomer with high purity, it is essential to repeat the purification process such as recrystallization several times, and thus the resulting yield becomes usually reduced.

International Patent Publication No. WO 98/051689 discloses a method to overcome the above drawbacks, which is summarized and represented by the following scheme 2:

[Scheme 2]

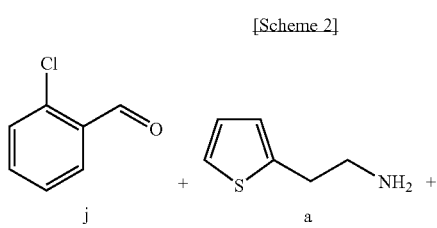

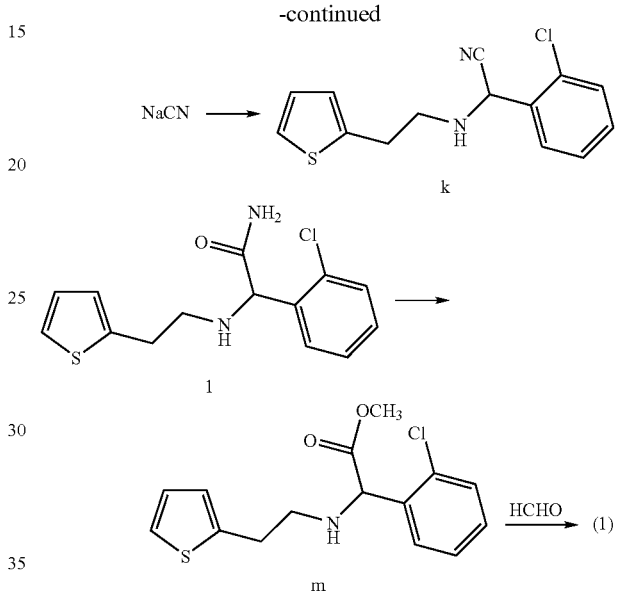

In the conventional process according to scheme 2, 2-(2-thienyl)-ethylamine of formula (a) in scheme 2 is reacted with o-chlorobenzaldehyde of formula (j) in scheme 2 and sodium cyanide. The resulting nitrile compound of formula (k) in scheme 2 is converted into an amide compound corresponding to formula (l) in scheme 2 and then converted into a methyl ester compound of formula (m) in scheme 2. An intermediate (m) that is an appropriate form used for the synthesis of clopidogrel may be prepared by reacting with an optically active acid through an optical separation of amide (l) or ester (m). Finally, the optical isomer of formula (m) in scheme 2 is subjected to cyclization with formaldehyde in an acidic medium, thereby preparing clopidogrel.

European Patent No. 0466569 discloses another conventional process, which is summarized and expressed by the following scheme 3:

[Scheme 3]

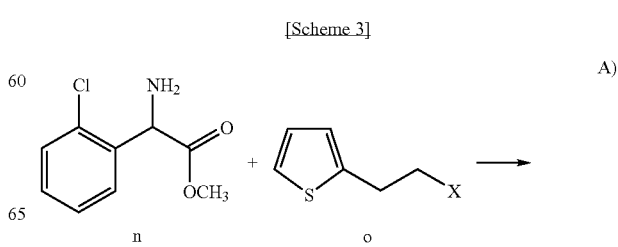

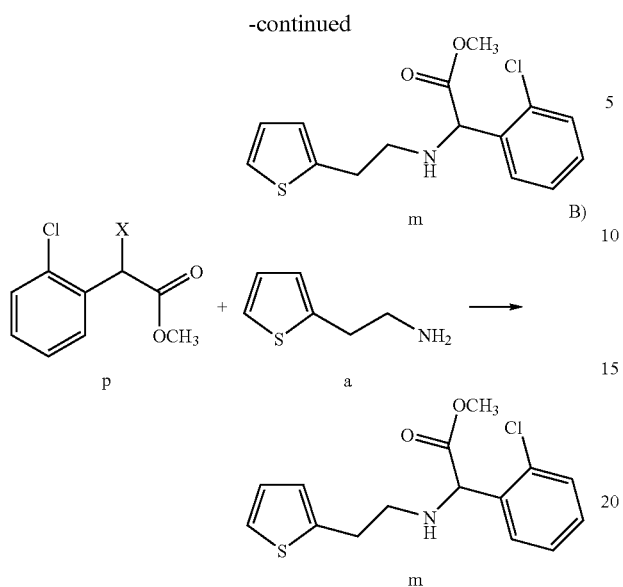

wherein X is a halogen or a sulfonate group.

In the conventional process according to above scheme 3, methyl 2-amino-(2-chlorophenyl)acetate of formula (n) in scheme 3 is reacted with 2-(2-thienyl)ethanol derivative of formula (o) in scheme 3 to prepare an intermediate of formula (m) in scheme 3 (Process A), or methyl 2-halo-(2-chlorophenyl)acetate of formula (p) in scheme 3 is reacted with 2-(2-thienyl)-ethylamine of formula (a) in scheme 3 to obtain an intermediate of formula (m) in scheme 3 (Process B).

Moreover, International Patent Publication No. WO 99/018110 discloses a process for the preparation of clopidogrel by a reaction between tetrahydrothienopyridine (r) and (R)-2-chloromandelic acid ester with a sulfonate leaving group (q) as shown in the following scheme 4.

[Scheme 4]

However, the conventional process according to scheme 4 using 4,5,6,7-tetrahydro[3,2-c]thienopyridine of formula (r) in scheme 4 has a drawback that it is difficult to be purified by crystallization since it has a low melting point and is readily dissolved in an organic solvent.

As described above, the conventional processes for the preparation of clopidogrel are known to have numerous drawbacks.

Accordingly, an object of the present invention is to provide a process for the preparation of S-(+)-clopidogrel with high optical and chemical purity in a simple manner that a diastereomeric salt is formed from a racemic carboxylic acid intermediate of clopidogrel using a (+)-cinchonine by an optical resolution and then by extraction with a suitable solvent.

DISCLOSURE

As represented by the following scheme 5, the present invention provides a process for the preparation of S-(+)-clopidogrel, which includes the steps of:

(1) preparing a diastereomeric salt represented by the following formula 4 by reacting a racemic carboxylic acid of clopidogrel represented by the following formula 2a with a (+)-cinchonine represented by the following formula 3;

(2) preparing a carboxylic acid of an S-(+)-clopidogrel represented by the following formula 2b by treating the diastereomeric salt represented by the following formula 4 under an acidic condition; and (3) preparing an S-(+)-clopidogrel represented by the following formula 1 by reacting the carboxylic acid of S-(+)-clopidogrel represented by the following formula 2b with methanol under an acidic condition.

[Scheme 5]

-continued

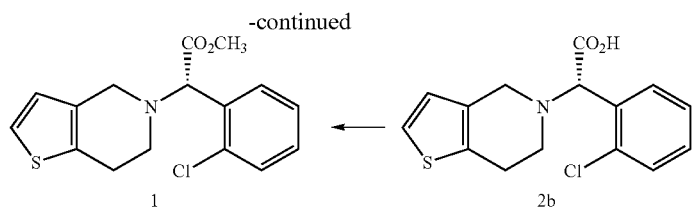

Hereinafter, the preparation process in accordance with the present invention will be described in more detail.

Step (1) is directed to a process of forming a diastereomeric salt represented by the above formula 4 by reacting a racemic carboxylic acid of clopidogrel represented by the above formula 2a with a (+)-cinchonine represented by the above formula 3.

The racemic carboxylic acid of clopidogrel represented by the above formula 2a used as a starting material in the preparation process of the present invention is a racemic mixture that can be readily obtained by hydrolyzing the racemic clopidogrel in a general method. The (+)-cinchonine represented by the above formula 3 used in the present invention has a chemical purity of more than 85% and contains dihydrocinchonine of less than 15%.

The (+)-cinchonine represented by the formula 3 may be used in a range of 0.5 to 1 equivalent per equivalent of the racemic carboxylic acid of clopidogrel represented by the formula 2a, and the ratio of the carboxylic acid isomer of (R)-clopidogrel contained in a mother liquor to the cinchonine salt may be varied according to the equivalent ratio of the (+)-cinchonine applied thereto. Here, the reaction solvent used in the present invention may be a single solvent selected from the group consisting of water, ketones, alcohols, ethers, amides, esters, hydrocarbons, chlorohydrocarbons and nitrites, or a mixture thereof. Preferably, ketones, alcohols, nitrites or a mixture thereof may be used.

The optical resolution of the present invention is achieved by the formation of the diastereomeric salt in which the (+)-cinchonine is used as an optical resolution agent. More specifically, after reacting the racemic carboxylic acid of clopidogrel with the (+)-cinchonine, the resulting compound is subjected to stirring or shaking followed by standing using the above-mentioned organic solvent. Here, the temperature is preferably −30 to 60° C., and more preferably −10 to 40° C.

Step (2) is directed to a process of preparing a carboxylic acid of S-(+)-clopidogrel represented by the above formula 2b from the diastereomeric acid represented by the above formula 4.

That is, after dissolving the diastereomeric acid represented by the formula 4 in water, an acid is added to adjust the pH of the mixed solution to 3-5 for its acidification and then the carboxylic acid of S-(+)-clopidogrel represented by the formula 2b is extracted using a conventional organic solvent. The acid used to acidify the solution may be appropriately selected from inorganic acids such as hydrochloric acid, sulfuric acid, nitric acid, etc., or organic acids such as acetic acid, etc. The organic solvent used for the extraction may be a single solvent selected from the group consisting of water, ketones, alcohols, ethers, amides, esters, hydrocarbons, chlorohydrocarbons and nitrites, or a mixture thereof. Preferably, it is possible to use a single solvent selected from the group consisting of acetone, acetonitrile, methanol, ethanol, isopropanol, n-butanol, t-butanol, ethylacetate, dichloromethane, toluene, diethylether and n-hexane, or a mixture thereof.

The carboxylic acid of S-(+)-clopidogrel represented by the formula 2b obtained by the extraction using the above organic solvent may be obtained readily with high purity via a conventional filtration method. To obtain a carboxylic acid of (S)-(+)-clopidogrel with a higher optical purity as occasion demands, the optical purity can be increased by recrystallization under the condition of using an organic solvent containing acetone or acetonitrile used in the optical resolution.

Step (3) is directed to a process of preparing an S-(+)-clopidogrel represented by the formula 1 in accordance with the present invention by reacting the carboxylic acid of S-(+)-clopidogrel represented by the formula 2a with methanol under an acidic condition. That is, the S-(+)-clopidogrel represented by the formula 1 of the present invention is prepared by reacting the carboxylic acid of S-(+)-clopidogrel represented by the formula 2a with methanol under an acidic condition, where an organic acid such as thionyl chloride and the like is used 1.0 to 2.0 equivalents, at 40-80° C., preferably, at a reflux temperature.

While the preparation process of the present invention has been described in detail above by subdividing the process into the respective steps, the process for the preparation of (S)-(+)-clopidogrel performed continuously without the step of separating the intermediate produced in step (1), (2) or (3) may be included in the scope of the present invention.

Moreover, the (S)-(+)-clopidogrel of formula 1 obtained by the above-described preparation process may be prepared as a pharmaceutically acceptable salt by a general method. That is, it is possible to form pharmaceutically acceptable salts along with organic or inorganic acids such as hydrochloric acid, bromic acid, sulfuric acid, phosphoric acid, acetic acid, citric acid, fumaric acid, lactic acid, maleic acid, succinic acid, tartaric acid and the like, or prepare a pharmaceutically acceptable salt by reacting with alkali metal ions, such as sodium, potassium, etc., or with ammonium ions.

BEST MODE

The present invention as described above will be described in more detail based on the following examples; however, they should not be construed as limiting the scope of the present invention.

Example 1

Synthesis of Diastereomeric Salt (4) from Racemic Carboxylic Acid of Clopidogrel (2a)

3.078 g (10 mmol) of racemic carboxylic acid of clopidogrel (2a) and 3.47 g (10 mmol) of 85% (+)-cinchonine were placed into a 250 mL flask and completely dissolved by adding 100 mL of a mixed solution of ethanol:acetonitrile (1:2) thereto. After shaking the resulting solution at room temperature for 18 hours, the precipitate formed thereof was filtered under reduced pressure and then dried under vacuum at room temperature to obtain 1.74 g of diastereomeric salt (4) as a white solid.

Theoretical yield 58%; optical purity 98.9% (HPLC); $^1$H NMR (300 MHz, DMSO-$d_6$) δ 8.85 (d, 1H, J=4.5 Hz), 8.28 (d, 1H, J=8.1 Hz), 8.02 (dd, 1H, J=8.1 Hz, 1.2 Hz), 7.24-7.76 (m, 8H), 6.74 (d, 1H, J=5.1 Hz), 6.01-6.13 (m, 1H), 5.58 (d, 1H, J=5.1 hz), 5.14 (d, 1H, J=9.3 Hz), 5.09 (s, 1H), 4.64 (s, 1H), 3.56-3.73 (m, 2H), 3.25-3.32 (m, 2H), 2.66-2.90 (m, 7H), 2.28-2.34 (m, 1H), 1.95-2.03 (m, 1H), 1.75 (brs, 1H), 1.50-1.58 (m, 2H), 1.32-1.36 (m, 1H).

Example 2

Synthesis of Diastereomeric Salt (4) from Racemic Carboxylic Acid of Clopidogrel (2a)

3.078 g (10 mmol) of racemic carboxylic acid of clopidogrel (2a) and 1.735 g (5 mmol) of 85% (+)-cinchonine were placed into a 250 mL flask and completely dissolved by adding a mixed solution of 100 mL of ethanol:acetonitrile (1:2) thereto. After shaking the resulting solution at room temperature for 18 hours, the precipitate thus formed was filtered under reduced pressure and then dried under vacuum at room temperature to obtain 2.42 g of the diastereomeric salt (4) as a white solid.

Theoretical yield 80%; optical purity 99.8% (HPLC)

Example 3

Synthesis of Diastereomeric Salt (4) from Racemic Carboxylic Acid of Clopidogrel (2a)

3.078 g (10 mmol) of racemic carboxylic acid of clopidogrel (2a) and 3.078 g (10 mmol) of 85% (+)-cinchonine were placed into a 250 mL flask and completely dissolved by adding a mixed solution of 100 mL of ethanol:acetone (1:2) thereto. After shaking the resulting solution at room temperature for 18 hours, the precipitate thus formed was filtered under reduced pressure and then dried under vacuum at room temperature to obtain 2.54 g of the diastereomeric salt (4) as a white solid.

Theoretical yield 84%; optical purity 99.8% (HPLC)

Example 4

Synthesis of Diastereomeric Salt (4) from Racemic Carboxylic Acid of Clopidogrel (2a)

3.078 g (10 mmol) of racemic carboxylic acid of clopidogrel (2a) and 1.735 g (5 mmol) of 85% (+)-cinchonine were placed into a 250 mL flask and completely dissolved by adding a mixed solution of 100 mL of isopropanol:acetone (1:4) thereto. After shaking the resulting solution at room temperature for 18 hours, the precipitate thus formed was filtered under reduced pressure and then dried under vacuum at room temperature to obtain 2.32 g of the diastereomeric salt (4) as a white solid.

Theoretical yield 77%; optical purity 99.2% (HPLC)

Example 5

Synthesis of Carboxylic Acid of S-(+)-Clopidogrel (2b) from Diastereomeric Salt (4)

2.4 g (4 mmol) of the diastereomeric salt (4) synthesized in example 2 was mixed with water of 30 mL and c-HCL was dropwisely added slowly to adjust pH to 4. The organic layer extracted with dichloromethane (60 mL×3 times) was dried with $Na_2SO_4$ and filtered and then concentrated to give 1.12 g of carboxylic acid of S-(+)-clopidogrel (2b).

Yield 91%; optical purity 99.2% (HPLC); $^1$H NMR (300 MHz, $CDCl_3$) δ9.16 (brs, 1H), 7.96-7.99 (m, 1H), 7.38-7.43 (m, 1H), 7.25-7.30 (m, 2H), 7.16 (d, 1H, J=5.1 Hz), 6.66 (d, 1H, J=5.1 Hz), 5.24 (s, 1H), 4.17-4.31 (m, 2H), 3.52-3.57 (m, 1H), 3.30-3.32 (m, 1H), 3.04 (brs, 2H).

The optical purifies of the compounds synthesized in examples 1 to 5 were measured by chiral HPLC and the HPLC conditions applied to the separation are as follows:

Column: Ultron ES-OVM (Ovomucoid product), 150×4.6 mm, 5.0 mm
Flow rate: 1 mL/min
Detection wavelength: 220 nm
Eluate: methanol/dibasic sodium phosphate buffer solution (2 nM, pH 7.5) (5/95, v/v)
Sample: dissolved in a mixed solution of 0.1 mg/mL of the methanol/dibasic sodium phosphate buffer solution (2 nM, pH 7.5) (5/95, v/v) and added 10 mL thereto.

Example 6

Synthesis of S-(+)-Clopidogrel (1) from Carboxylic Acid of S-(+)-Clopidogrel (2b)

20 mL of methanol was added to 1.1 g (3.6 mmol) of the carboxylic acid of S-(+)-clopidogrel (2b) synthesized in example 5 to be dissolved. 0.32 mL of $SOCl_2$ was added to the resulting solution and stirred at 70° C. for 6 hours. Then, the resulting solution was cooled to room temperature and concentrated under reduced pressure and then 10% $NaHCO_3$ (aq.) was added to adjust pH to 7. The organic layer extracted with dichloromethane (20 mL×2 times) was dried with $Na_2SO_4$ and filtered and then concentrated under reduced pressure. After dissolving the resulting oil in dichloromethane, the resulting solution was passed through a small amount of silica gel column and washed with ethylacetate:n-hexane (1:6). Then, the resultant was dried under vacuum at room temperature to obtain 1.01 g of (S)-(+)-clopidogrel (1) as a pale yellow oil.

Yield 88%; optical purity 99.2% (HPLC); $^1$H NMR (300 MHz, $CDCl_3$) δ 7.68-7.71 (m, 1H), 7.39-7.43 (m, 1H), 7.27-7.30 (m, 2H), 7.06 (d, 1H, J=5.1 Hz), 6.67 (d, 1H, J=5.1 Hz), 4.92 (s, 1H), 3.73 (s, 3H), 3.61-3.78 (m, 2H), 2.88 (brs, 4H).

Example 7

Synthesis of (S)-(+)-Clopidogrel (1) from Racemic Carboxylic Acid of Clopidogrel (2a) by Successive Reactions 3.078 g (10 mmol) of racemic carboxylic acid of clopidogrel (2a) and 1.735 g (5 mmol) of 85% (+)-cinchonine were placed into a 250 mL flask and completely dissolved by adding a mixed solution of 120 mL of isopropanol:acetonitrile (1:2) thereto. After shaking the resulting solution at room temperature for 18 hours, the precipitate thus formed was filtered under reduced pressure and then dried under vacuum at room temperature to obtain 2.4 g of the diastereomeric salt (4) as a white solid.

2.4 g (4 mmol) of the diastereomeric salt (4) obtained as above was mixed with water of 30 mL and c-HCL was dropwisely added slowly to adjust pH to 4. The organic layer extracted with dichloromethane (60 mL×3 times) was dried with $Na_2SO_4$ and filtered and then concentrated.

20 mL of methanol was added to the concentrate containing the carboxylic acid of S-(+)-clopidogrel (2b) obtained as above to be dissolved. 0.35 mL of $SOCl_2$ was added to the resulting solution and stirred at 70° C. for 6 hours. Then, the resulting solution was cooled to room temperature and concentrated under reduced pressure and then 10% $NaHCO_3$(aq) was added to adjust pH to 7. The organic layer extracted with dichloromethane (20 mL×2 times) was dried with $Na_2SO_4$ and filtered and then concentrated under reduced pressure. After dissolving the resulting oil in dichloromethane, the resulting solution was passed through a small amount of silica gel column and washed with ethylacetate:n-hexane (1:6). Then, the resultant was dried under vacuum at room temperature to obtain 0.97 g of the (S)-(+)-clopidogrel (1) as a pale yellow oil.

Total yield 60%; optical purity 99.3%; $^1H$ NMR (300 MHz, $CDCl_3$) δ 7.68-7.71 (m, 1H), 7.39-7.43 (m, 1H), 7.27-7.30 (m, 2H), 7.06 (d, 1H, J=5.1 Hz), 6.67 (d, 1H, J=5.1 Hz), 4.92 (s, 1H), 3.61-3.78 (m, 5H), 2.88 (s, 4H).

The optical purities of the compounds synthesized in examples 6 to 7 were measured by chiral HPLC and the HPLC conditions applied to the separation are as follows:
- Column: Ultron ES-OVM (Ovomucoid product), 150×4.6 mm, 5.0 mm
- Flow rate: 1 mL/min
- Detection wavelength: 220 nm
- Eluate: dibasic sodium phosphate buffer solution (20 nM, pH 7)/acetonitrile (80/20, v/v)
- Sample: dissolved in a mixed solution of 0.1 mg/mL of the dibasic sodium phosphate buffer solution (20 nM, pH 7)/acetonitrile (80/20, v/v)

INDUSTRIAL APPLICABILITY

As described in detail above, the present invention can readily prepare the S-(+)-clopidogrel with high optical and chemical purity in such a manner that a diastereomeric salt is formed from a racemic carboxylic acid intermediate using a (+)-cinchonine by an optical resolution and then by extraction with a suitable solvent.

The invention claimed is:

1. A process for preparing S-(+)-clopidogrel comprising:

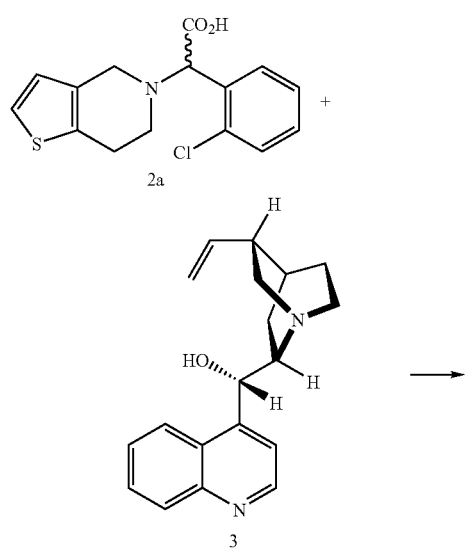

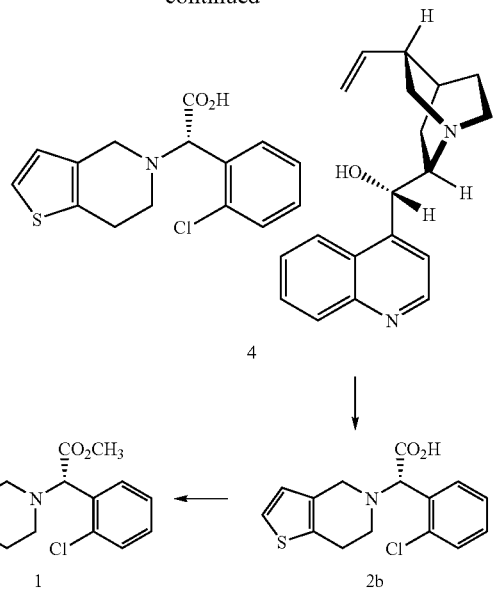

(1) preparing a diastereomeric salt represented by the above formula 4 by reacting a racemic carboxylic acid of clopidogrel represented by the above formula 2a with a (+)-cinchonine represented by the following formula 3;
(2) preparing a carboxylic acid of S-(+)-clopidogrel represented by the above formula 2b by treating the diastereomeric acid represented by the above formula 4 under an acidic condition; and
(3) preparing an S-(+)-clopidogrel represented by the above formula 1 by reacting the carboxylic acid of S-(+)-clopidogrel represented by the above formula 2a with methanol under an acidic condition.

2. In claim 1, the (+)-cinchonine represented by the above formula 3 is used in a range of 0.5 to 1 equivalent per 1 equivalent of the racemic carboxylic acid of clopidogrel represented by the above formula 2a.

3. In claim 1, the carboxylic acid of S-(+)-clopidogrel represented by the above formula 2b is optically resolved by extraction using a single solvent selected from the group consisting of water, ketones, alcohols, ethers, amides, esters, hydrocarbons, chlorohydrocarbons and nitriles, or a mixture thereof.

4. In claim 3, the solvent used in the optical resolution contains acetone or acetonitrile.

5. In claim 3, the optical resolution is achieved by stirring (or shaking) and standing the reactant mixture.

6. In claim 3, the optical resolution is carried out at a temperature of from −30 to 60° C.

7. In claim 1, the carboxylic acid of S-(+)-clopidogrel represented by the following formula 2b is recrystallized to increase optical purity.

8. In claim 7, the recrystallization solvent contains acetone or acetonitrile.

9. In claim 1, the steps of (1), (2) and (3) are performed continuously without separating an intermediate.

10. In claim 4, the optical resolution is carried out at a temperature of from −30 to 60° C.

11. In claim 5, the optical resolution is carried out at a temperature of from −30 to 60° C.

12. In claim 3, the carboxylic acid of S-(+)-clopidogrel represented by the following formula 2b is recrystallized to increase optical purity.

* * * * *